United States Patent [19]

Schultz et al.

[11] 4,215,070
[45] Jul. 29, 1980

[54] N-(PHOSPHONOACETYL)-L-ASPARTIC ACID COMPOUNDS AND METHODS FOR THEIR PREPARATION

[75] Inventors: Robert J. Schultz, Amherst; Fred W. Starks, Kenmore, both of N.Y.

[73] Assignee: Starks Associates, Inc., Buffalo, N.Y.

[21] Appl. No.: 954,579

[22] Filed: Oct. 25, 1978

Related U.S. Application Data

[63] Continuation-in-part of Ser. No. 932,501, Aug. 10, 1978, which is a continuation-in-part of Ser. No. 851,382, Nov. 14, 1977, abandoned.

[51] Int. Cl.$^2$ .................................................. C07F 9/38
[52] U.S. Cl. .................................... 260/502.5; 544/358
[58] Field of Search .............. 560/171; 260/942, 502.5; 544/357, 358

[56] References Cited

U.S. PATENT DOCUMENTS 4,154,759   5/1979   Parsons et al. .................... 260/502.5

*Primary Examiner*—Jose Tovar
*Attorney, Agent, or Firm*—Holman & Stern

[57] ABSTRACT

N-(Phosphonoacetyl)-L-aspartic acid (PALA) compounds, especially novel PALA compounds, and methods for their preparation in large amounts are disclosed. These methods include preparation of certain PALA compounds such as PALA dibenzyl ester, disodium PALA, and the cyclohexylamine salt of dibenzyl PALA.

1 Claim, No Drawings

N-(PHOSPHONOACETYL)-L-ASPARTIC ACID COMPOUNDS AND METHODS FOR THEIR PREPARATION

The invention described herein was made in the course of work under a grant or award from the Department of Health, Education and Welfare.

BEFORE BACKGROUND AND SUMMARY OF THE INVENTION

This application is a continuation-in-part of application Ser. No. 932,501 filed Aug. 10, 1978, which in turn is a continuation-in-part of application Ser. No. 851,382 filed Nov. 14, 1977 and now abandoned.

BACKGROUND AND SUMMARY OF THE INVENTION

The free tetra acid, N-(phosphonoacetyl)-L-aspartic acid (sometimes referred to herein as PALA), is a known compound. The present invention relates to novel N-(phosphonoacetyl)-L-aspartic acid (PALA) compounds, especially disodium PALA, and to methods for preparation of N-(phosphonoacetyl)-L-aspartic acid compounds. A particular aspect of the present invention is concerned with the large-scale preparation of the known tetrasodium salt and the novel disodium salt of N-(phosphonoacetyl)-L-aspartic acid.

The known tetra acid compound, N-(phosphonoacetyl)-L-aspartic acid (PALA), was first prepared by Stark et al., *J. Biol. Chem.*, 246, 6599 (1971). The tetrasodium salt of PALA is a known antitumor agent, as reported in the literature, particularly *Cancer Research*, 36, 2720 (1976), incorporated herewith by reference. For example, the survival time of mice bearing intraperitoneal P388 leukemia was prolonged by up to 64% (when treated with PALA tetrasodium salt in a dose range of 188 to 750 mg./kg., i.p.). Lewis lung sarcoma was highly sensitive to PALA tetrasodium salt in mice at i.p. doses from 240 to 490 mg./kg. Mice bearing B16 melanoma survived 77 to 86% longer than did controls when treated with PALA tetrasodium salt (490 mg./kg., i.p.).

While the synthesis of the tetra acid PALA is straight-forward, the preparation of the tetrasodium salt, especially in kilogram quantities, has proven to be a major problem. The methods of the present invention are particularly well-suited for the production of such quantities.

DESCRIPTION OF THE PREFERRED EMBODIMENTS

The novel PALA compounds of the invention are N-(phosphonoacetyl)-L-aspartic acid, disodium salt, and the corresponding P-ethyl ester and dibenzyl ester;

N-(phosphonoacetyl)-L-aspartic acid, dibenzyl ester, and the corresponding N,N'-dibenzylethylenediamine salt and cyclohexylamine salt;

N-(phosphonoacetyl)-L-aspartic acid, tetraethyl ester and the corresponding dimethyl P,P-diethyl ester;

N-(phosphonoacetyl)-L-aspartic acid, calcium salt; and

The piperazine salt and cyclohexylamine salt of N-(phosphonoacetyl)-L-aspartic acid.

The novel compounds of the invention either possess anti-tumor activity in vivo or are intermediates which can advantageously be used for the production of active antitumor PALA compounds or, unlike the known PALA tetrasodium salt, are relatively non-hygroscopic substances or are mobile, free-flowing particulate solids.

Some of these novel PALA compounds exist in anhydrous form, some in solvated (including hydrated) form. Both forms are suitable for purposes of the invention. The disodium PALA compound produced by the methods of the invention is a hydrate, differing from one preparation to another in the content of water of hydration, typically from about 0.2 to 2 moles of water. The compound also may contain as a solvate ethanol (e.g., from about 0.1 to 0.5 mole), acetic acid (e.g., from about 0.03 to 0.4 mole) and sodium acetate (e.g., about 0.2 mole). The acetic acid and ethanol can be removed by freeze-drying. Two to three lyophilizations afford solvent free material. The disodium PALA compound produced by these methods may also contain substantial amounts of trisodium PALA including as much as 30 to 40% trisodium PALA. All of such solvates of disodium PALA and mixtures of disodium PALA and trisodium PALA are intended to be included within the term disodium PALA (or equivalent term) as used herein since these product forms are interchangeable for use as the active antitumor ingredient of formulations contemplated by the invention. For use as an antitumor agent, the novel disodium PALA is substantially equivalent in activity and toxicity to the known tetrasodium PALA. Disodium PALA can be used for its antitumor activity, according to the invention, in the form of pharmaceutical compositions and a compatible pharmaceutically acceptable carrier. The compositions may also contain antimicrobial agents and other antitumor agents. The compositions may be made up in any pharmaceutical form appropriate for the route of administration in question. Examples of such compositions include solid compositions for oral administration such as tablets, capsules, pills, powders and granules, liquid compositions for topical or oral administration such as solutions, suspensions, syrups and elixirs, and preparations for parenteral administration such as sterile solutions, suspensions or emulsions. For use as an antitumor agent, the compositions are administered in a dosage regimen such that the tumor growth is inhibited. A suggested dosage regimen for use as an antitumor agent (especially for solid tumors as described above) in mammalian species is 50 to 500 mg. of disodium PALA per kilogram for a single daily parenteral (e.g., intravenous infusion, as a 2% aqueous solution) treatment course. The novel calcium salt of PALA is equivalent pharmaceutically for the purposes of the invention to disodium PALA and thus can be used in place of or in combination with disodium PALA in the above-described compositions. The calcium salt of PALA has favorable solubility properties; it dissolves in water permitting ready formulation yet it dissolves relatively slowly thus allowing for water wash removal of soluble inorganic impurities.

The novel disodium PALA advantageously is a mobile, free-flowing particulate solid which can readily be handled, analyzed and weighed for formulation purposes. By comparison with the known tetrasodium PALA, it is relatively nonhygroscopic. Tetrasodium PALA absorbs atmospheric moisture 1.5 times faster than disodium PALA and is difficult to handle and analyze. Whereas tetrasodium PALA is water-soluble, disodium PALA advantageously has a solubility in water of greater than 950 mg./ml. Disodium PALA as a 2% (w./v.) solution in water characteristically has a pH of about 4; comparable trisodium PALA and tetrasodium PALA solutions have a pH of about 6 and about 9, respectively. Disodium PALA is also characterized by a 60-Mc. nuclear magnetic resonance (nmr) spectrum which typically shows a doublet corresponding to the methylene group (—$CH_2$) which is alpha to the —CH group whereas tetrasodium PALA characteristically has an nmr spectrum which shows a 3 line multiplet corresponding to the mentioned methylene group.

The PALA tetraethyl ester and PALA dimethyl ester, P,P-diethyl ester are readily obtained in anhydrous form and give elemental analyses with excellent agreement between the found and calculated values. For example, the maximum difference between calculated and found values of hydrogen for these tetraesters is 0.03% compared with a maximum 1.27% difference for tetrasodium PALA.

Cyclohexylamine and piperazine form solid PALA salts. In addition, the cyclohexylamine salt is completely non-hygroscopic.

One embodiment of the invention, in a method for the preparation of PALA compounds, comprises the steps of reacting L-aspartic acid with benzyl alcohol and p-toluenesulfonic acid to obtain L-aspartic acid, dibenzyl ester p-toluenesulfonate, reacting the L-aspartic acid, dibenzyl ester p-toluenesulfonate with triethylamine, adding phosphonoacetyl chloride to produce PALA dibenzyl ester; and separating the PALA dibenzyl ester from unreacted phosphonoacetyl chloride. The PALA dibenzyl ester is separated in any suitable way. Since it is insoluble in water, the PALA dibenzyl ester and unreacted phosphonoacetyl chloride preferably are separated by washing the reaction mixture with water to remove the phosphonoacetyl chloride.

According to another embodiment, the dibenzyl ester is subjected to hydrolysis with aqueous sodium hydroxide to obtain a product mixture containing tetrasodium PALA hereinafter referred to as the "product mixture".

Another embodiment comprises the steps of subjecting the product mixture to an ion exchange procedure to obtain N-(phosphonoacetyl)-L-aspartic acid in the free acid form, titrating said free acid to a pH of 9.2 and recovering the purified tetrasodium salt.

Another embodiment comprises the steps of dissolving said product mixture in glacial acetic acid, diluting the resulting solution with ethanol to precipitate the disodium PALA, and recovering said disodium PALA.

Another embodiment comprises the steps of reacting PALA dibenzyl ester with N,N'-dibenzylethylenediamine to produce the N,N'-dibenzylethylenediamine salt of the PALA dibenzyl ester, subjecting said salt to hydrolysis to produce a product mixture containing the PALA tetrasodium salt, dissolving said product mixture in glacial acetic acid, diluting the resulting solution with ethanol to precipitate the PALA disodium salt, and recovering said PALA disodium salt.

Another embodiment comprises using perchloroethylene as the esterification medium in the reaction of L-aspartic acid with benzyl alcohol and p-toluenesulfonic acid monohydrate. In preparing dibenzyl aspartate, perchloroethylene was the solvent of choice. It forms an excellent azeotrope with water; it boils high enough that the large-scale esterification is soon completed (within 3 hours) and, at the same time, the product stability is not affected by the temperature—at least during this short time of thermal contact.

Another embodiment—in a method for the preparation of PALA compounds, including the steps of reacting PALA dibenzyl ester, cyclohexylamine salt with sodium hydroxide to produce L-aspartic acid, N-(phosphonoacetyl)-, tetrasodium salt, and reacting said tetrasodium salt with acetic acid to produce disodium PALA—comprises precipitating the obtained disodium salt twice from water, the second precipitation including adding an aqueous solution of said disodium salt dropwise to a vortex of vigorously stirred ethanol, thereby removing impurities in the form of acetic acid and sodium acetate.

The production of disodium PALA according to the invention offers the following advantages: (1) a shorter time is required to synthesize the material due to (a) complete elimination of ion exchange columns, and (b) substantial reduction in the volume of water required to be evaporated; (2) the projected cost for 5 kg. amounts of material is at least 30% less than that for 5 kg. of tetrasodium PALA; (3) the consistently low hydrogen analyses associated with tetrasodium PALA are no longer a problem; (4) the synthesis is readily adaptable to scale-up; (5) the product obtained is less hygroscopic than tetrasodium PALA and, unlike tetrasodium PALA, is a mobile, free flowing particulate solid which can be readily handled and weighed for formulation purposes; and (6) the material is extremely water soluble.

Another embodiment, in a method for the preparation of a PALA compound, comprises the steps of reacting L-aspartic acid, dibenzyl ester p-toluenesulfonate with triethylamine, adding phosphonoacetyl chloride to produce PALA dibenzyl ester, and reacting said dibenzyl ester with cyclohexylamine to produce the cyclohexylamine salt of said dibenzyl ester.

The following examples are illustrative of the present invention.

EXAMPLE 1

L-Aspartic acid, dibenzyl ester p-toluenesulfonate (I)

A stirred mixture of L-aspartic acid (399 g.; 3.00 moles), benzyl alcohol (1.95 kg.; 18.0 moles), p-toluenesulfonic acid monohydrate (582 g.; 3.06 moles), and dry benzene (1.2 l.) was heated at reflux for 16 hours. The water formed in the reaction (145 ml.) was removed by means of a Dean-Stark trap. The resulting solution was cooled to room temperature, then diluted with benzene (1.2 l.) and ether (3.6 l.). The resulting solid was collected on a filter, washed with ether (7.0 l.), and dried; yield, 1195 g. (82%). The crude product was recrystallized from methanol (1720 ml.) to give 959 g. (80% recovery) of purified (I); m.p., 158°–159.5°; literature m.p., 158°–160°. Additional reactions were carried out to give a total of 4.27 kg. of product suitable for further transformation.

Phosphonoacetic acid (II)

A stirred solution of triethyl phosphonoacetate (900 g.; 4.01 moles) in 6 M hydrochloric acid (6.1 l.) was heated at reflux for 6.5 hours. The solution was concentrated in vacuo, then last traces of water were removed by co-evaporation with benzene (2×300 ml.). The solid residue was recrystallized twice from 1.0 l. of glacial acetic acid to give 342 g. (60.8%) of acid (II); m.p., 140°–141°; literature m.p., 143°. Additional reactions were carried out to give a total of 1020 g. of product suitable for further transformation.

Phosphonoacetychloride (III)

A stirred mixture of phosphonoacetic acid (II) (355 g.; 2.54 moles) and thionyl chloride (1770 ml.) was heated at 50°–55° for 4.5 hours. The resulting solution was concentrated in vacuo (<35°; aspirator pressure then 1 mm. Hg) to give 395.7 g. (98.3%) of product. The yellow, oily material was used in the following reaction without further characterization.

L-Aspartic acid, N-(phosphonoacetyl)-, dibenzyl ester (IV)

To a cool (15°), stirred suspension of L-aspartic acid, dibenzyl ester p-toluenesulfonate (I) (812 g.; 1.67 moles) in dry dioxane (5.2 l.) was added, dropwise, triethylamine (486 g.; 4.80 moles) during 30 minutes. The resulting solution was stirred at 15° for 30 minutes, then phosphonoacetyl chloride (III) (395.7 g.; 2.500 moles) dissolved in dry dioxane (600 ml.) was added, dropwise, during 1 hour. The temperature was maintained below 15° during the addition. The cooling bath was removed, and the reaction mixture was stirred for 1 hour. The insolubles were filtered off and washed with dioxane (2.0 l.). The filtrate was concentrated in vacuo, then the oily residue was dissolved in benzene (10.1 l.). The organic solution was washed with water (6×4.0 l.), dried over magnesium sulfide, then evaporated in vacuo to give 568 g. (78.1%) of product as a yellow, crusty solid suitable for further transformation.

L-Aspartic acid, N—(phosphonoacetyl)—, tetrasodium salt.4.5 H$_2$O (PALA) (VII)

To a cool (10°), stirred solution of sodium hydroxide (312 g.; 7.80 moles) in 10.0 l. of water was added, in one portion, L-aspartic acid, N—(phosphonoacetyl)—, dibenzyl ester (IV) (568 g.; 1.30 moles). The mixture was stirred at 10°–15° for 6 hours, then the insolubles were filtered off. The filtrate was concentrated in vacuo to a volume of 3.0 l. then extracted with methylene chloride (1×1.3 l.) and ether (1×1.3 l.). The aqueous solution was added to 12.0 l. of ethanol resulting in the precipitation of a semi-solid. After decantation, the material was dissolved in water (680 ml.), and equal portions of the solution were applied to two AG50W-X8 (hydrogen form) cation exchange resin columns (9.6 cm.×25 cm.). Each column was eluted with 2.0 l. of water (20 fractions of 100 ml. each). Fractions 7–14 of each column, which contained the desired product as determined by TLC, were combined and evaporated in vacuo (bath temperature<30°). The oily residue was dissolved in acetone (2.0 l.), charcoal (50 g.) was added, and the mixture was stirred at room temperature for 18 hours. The insolubles were filtered off, then the filtrate was evaporated in vacuo. The semi-solid residue (tetraacid; 227.1 g.) was dissolved in 2.0 l. of water. The stirred solution was cooled to 10° then titrated to pH 9.2 with 1 N aqueous sodium hydroxide (3123 ml.). The basic solution was concentrated at reduced pressure (1–2 mm. Hg; <30°), and the oily residue was triturated with acetone (5.8 l.). The solid material was partially dried in vacuo then triturated with acetone (2.0 l.) and ether (2.0 l.). The resulting powder was dried at reduced pressure over phosphorus pentoxide for 9 days at room temperature to give 272.2 g. of the desired product.

| Calc'd. for C$_6$H$_6$NO$_8$P | C | H | N | P | Na |
|---|---|---|---|---|---|
| . 4Na . 4.5 H$_2$O | 16.99 | 3.56 | 3.30 | 7.30 | 21.68 |
| Found | 16.76 | 2.29 | 3.46 | 7.31 | 21.61 |

Spectral Data:

Nuclear Magnetic Resonance (D$_2$O): δ 2.29 (m, 4, —CH$_2$ α to P+—CH$_2$ α to —CH); 4.13 (m, 1, —CH).

Optical Rotation:

| Observed | Literature |
|---|---|
| $[\alpha]_D^{25}$ + 9.44 (c, 3.743 in water) | $[\alpha]_D^{25}$ + 10.30 (c, 3.798 in water) |

Chromatography:

| Thin Layer Chromatography (Cellulose, Quanta/Gram Q2F Glass Plates) | |
|---|---|
| Solvent System | R$_f$ Value |
| 1. Ethanol-ammonium hydroxide-water (6:1:3) | 0.13 |
| 2. n-Butanol-acetic acid-water (5:2:3) | 0.30 (tailing) |
| 3. Lithium chloride (0.6 M)-ethanol-ammonium hydroxide (5:5:1) | 0.61 |
| 4. Ethanol-water (2:3) | 0.81 |

Quantity Spotted: 112 μg.

Detection: Phospray (A commercial reagent used to visualize phosphorus containing compounds).

Results: The compound moves as one spot in each of the solvent systems. TLC of the free acid, liberated from the tetrasodium salt with hydrochloric acid, gave a negative test for aspartic acid when sprayed with ninhydrin.

EXAMPLE 2

L-Aspartic acid, N—(phosphonoacetyl)—, disodium salt.1.1 H$_2$O

L-Aspartic acid, N—(phosphonoacetyl)—, tetrasodium salt-4.5 H$_2$O (VII)(10.0 g.; 0.236 mole) was dissolved in hot (90°), glacial acetic acid (125 ml.). Celite (5 g.) was added to the hot, cloudy solution, then the insolubles were filtered off. The clear, cooled, dark yellow filtrate was diluted with ethanol (300 ml.), and the resulting mixture was stirred at room temperature for 30 minutes. The precipitated solid was collected on a filter, washed by resuspension in ethanol (3×300 ml.) and ether (1×300 ml.), then dried to give 5.7 g. (80.8%) of the disodium salt as a white powder. An additional 5.0 g. of product was prepared in a similar manner. The combined material (10.7 g.), contaminated with acetic acid and ethanol (determined by N.M.R.), was dissolved in water (250 ml.). The aqueous solution was clarified by filtration then freeze-dried. The lyophilizing process was repeated two more times, then the product was dried to constant weight in vacuo at 40° over phosphorus pentoxide; yield of analytically pure product, 9.0 g. (84.1% recovery).

Anal.
Calc'd. for C$_6$H$_8$NO$_8$P . 2 Na . 1.1 H$_2$O

| | C | H | N | P | Na |
|---|---|---|---|---|---|
| | 22.60 | 3.22 | 4.39 | 9.71 | 14.42 |
| Found | 22.68 | 3.21 | 4.36 | 9.62 | 14.37 |

Spectral Data:

Nuclear Magnetic Resonance (D$_2$O): δ 2.75 (d, 2, J=20 Hz, —CH$_2$ α to P); 2.80 (d, 2, —CH$_2$ α to —CH); 4.53 (t, 1, —CH).

Optical Rotation:

Observed: $[\alpha]_D^{25} + 15.95$ (c, 2.000 in water).
Chromatography:

| | Thin Layer Chromatography (Cellulose, Quanta/Gram Q2F Glass Plates) | |
|---|---|---|
| | Solvent System | $R_f$ Value |
| 1. | Lithium chloride (0.6 M)-ethanol-ammonium hydroxide (5:5:1) | 0.47 |
| 2. | Ethanol-water (2:3) | 0.75 |
| 3. | n-Butanol-acetic acid-water (5:2:3) | 0.19 |

Detection: Phospray (A commercial spray reagent used to visualize phosphorus-containing compounds).
Results: The compound moves as one spot in each of the solvent systems.

EXAMPLE 3

L-Aspartic acid, N—(phosphonoacetyl)—, disodium salt, monohydrate.0.3 acetic acid.0.1 ethanol To 2.0 l. of hot (85°), glacial acetic acid was added, in one portion, L-aspartic acid, N—(phosphonoacetyl)—tetrasodium salt, tetrahydrate (VII)(214 g.; 0.516 mole). After stirring the mixture at 85°–90° for 30 minutes, Celite (50 g.) was added, then the insolubles were filtered off. The clear, dark yellow filtrate was cooled to room temperature and diluted with ethanol (4.5 l.). The resulting mixture was stirred for 30 minutes, then the precipitated solid was collected on a filter. The material was washed by resuspension in ethanol (2×3.5 l.) and ether (1×1.2 l.) then dried in vacuo at 55° over phosphorus pentoxide to give 111.8 g. (63.8%) of the analytically pure disodium salt.

Anal.
Calc'd. for $C_6H_8NO_8P \cdot 2\,Na \cdot H_2O \cdot 0.3\,C_2H_4O_2 \cdot 0.1\,C_2H_6O$

| | C | H | N | P | Na |
|---|---|---|---|---|---|
| | 24.04 | 3.50 | 4.12 | 9.12 | 13.53 |
| Found | 24.19 | 3.56 | 4.14 | 8.96 | 13.48 |

Spectral Data:

Nuclear Magnetic Resonance (D$_2$O): $\delta$ 0.92 (t, 0.3, —CH$_3$ of ethanol); 1.83 (s, 0.9, —CH$_3$ of acetic acid); 2.55 (d, 2, J=20 Hz, —CH$_2$ $\alpha$ to P); 2.58 (d, 2, —CH$_2$ $\alpha$ to —CH); 3.33 (q, 0.2, —CH$_2$ of ethanol); 4.32 (t, 1, —CH).

Optical Rotation:
Observed: $[\alpha]_D^{22} + 15.31$ (c, 2.103 in water).
Chromatography:

| | Thin Layer Chromatography (Cellulose, Quanta/Gram Q2F Glass Plates) | |
|---|---|---|
| | Solvent System | $R_f$ Value |
| 1. | Lithium chloride (0.6 M)-ethanol-ammonium hydroxide (5:5:1) | 0.54 |
| 2. | Ethanol-water (2:3) | 0.69 |
| 3. | Ethanol-ammmonium hydroxide-water (6:1:3) | 0.18 (elongated) |
| 4. | n-Butanol-acetic acid-water (5:2:3) | 0.20 (tailing) |

Detection: Phospray (A commercial spray reagent used to visualize phosphorus-containing compounds).
Results: The compound moves as one spot in each of the solvent systems.

EXAMPLE 4

L-Aspartic acid, N—(phosphonoacetyl)—, disodium salt, monohydrate.0.3 acetic acid.0.1 ethanol L-Aspartic acid, N—(phosphonoacetyl)—, tetrasodium salt.4.5 H$_2$O (VII)(716.8 g.; 1.690 moles) was added, in one portion, to hot (95°), glacial acetic acid (7.0 l.). The mixture was stirred at 90°–95° for 45 minutes, then Celite (250 g.) was added. After stirring the hot (90°–95°) mixture for 20 minutes, the insolubles were collected on a filter and washed with acetic acid (0.5 l.). The clear, dark orange filtrate was cooled to room temperature and diluted with ethanol (16.1 l.). The resulting mixture was stirred for 1 hour, then the precipitated solid was collected on a filter. The material was suspended in ethanol (7.5 l.), and the suspension was vigorously stirred for 3 hours. The solid was collected on a filter then washed as above with ethanol (2×7.5 l.) and ether (1×7.5 l.). The material was dried in vacuo at 50°–55° over phosphorus pentoxide to give 426.5 g. (74.3%) of the analytically pure disodium salt.

Anal.
Calc'd. for $C_6H_8NO_8P \cdot 2\,Na \cdot H_2O \cdot 0.3\,C_2H_4O_2 \cdot 0.1\,C_2H_6O$

| | C | H | N | P | Na |
|---|---|---|---|---|---|
| | 24.04 | 3.50 | 4.12 | 9.12 | 13.53 |
| Found | 24.35 | 3.46 | 4.19 | 8.78 | 13.44 |

Spectral Data:

Nuclear Magnetic Resonance (D$_2$O): $\omega$ 0.98 (t, 0.3, —CH$_3$ of ethanol); 1.88 (s, 0.9, —CH$_3$ of acetic acid); 2.61 (d, 2, J=20 Hz, —CH$_2$ $\alpha$ to P); 2.63 (d, 2, —CH$_2$ $\alpha$ to —CH); 3.44 (q, 0.2, —CH$_2$ of ethanol); 4.36 (t, 1, —CH)

Optical Rotation:
Observed: $[\alpha]_D^{22} + 14.86$ (c, 1.998 in water).
Chromatography:

| | Thin Layer Chromatography (Cellulose, Quanta/Gram Q2F Glass Plates) | |
|---|---|---|
| | Solvent System | $R_f$ Value |
| 1. | Lithium chloride (0.6 M) -ethanol-ammonium hydroxide (5:5:1) | 0.60 |
| 2. | Ethanol-water (2:3) | 0.78 |
| 3. | Ethanol-ammonium hydroxide-water (6:1:3) | 0.19 |
| 4. | n-Butanol-acetic acid-water (5:2:3) | 0.22 (elongated) |

Quantity Spotted: 80 $\mu$g.
Detection: Phospray (A commercial spray reagent used to visualize phosphorus-containing compounds).
Results: The compound moves as one spot in each of the solvent systems.

EXAMPLE 5

L-Aspartic acid, N—(Phosphonoacetyl)—, dibenzyl ester. N,N'-dibenzylethylenediamine Salt (XII)

To a cool (5°), stirred solution of L-aspartic acid, N—(phosphonoacetyl)—, dibenzyl ester (IV)(2449 g.; 5.625 moles) in methylene chloride (9.5 l.) was added, dropwise, N,N'-dibenzylethylenediamine (1488 g.; 6.191 moles) dissolved in methylene chloride (1.65 l.) during 3.0 hours. The temperature was maintained below 15° during the addition. After removing the cooling bath, the reaction solution was stirred at room temperature for 16 hours then concentrated in vacuo to an oil. The residue was dissolved in acetone (5.0 l.), and the solution was stored overnight (18 hours) at room temperature. A finely divided, white solid, which had precipitated from solution, was filtered off, then the filtrate was evaporated at reduced pressure. The crude material was dissolved in ethyl acetate (12.0 l.). The organic solution was washed with water (3×3.5 l.), dried over magnesium sulfate, stirred with Norit A (125 g.) for 45 minutes, then spin-evaporated in vacuo. The residue ("glass") was triturated to a powder by vigorous stirring with ether-petroleum ether (b.p., 30°-60°) (5.0 l.: 7.0 l.). The solid product was collected on a filter then dried to give 1609 g. of the tan colored salt; m.p., >300°. An additional reaction was carried out in a similar manner to give a total of 2308.5 g. of (XII) suitable for the further transformation.

L-Aspartic acid, N—(phosphonoacetyl)—, tetrasodium salt (V)

To a cool (14°), stirred solution of sodium hydroxide (240 g.; 6.00 moles) in water (7.8 l.) was added, in portions, thoroughly pulverized L-aspartic acid, N-(phosphonoacetyl), dibenzyl ester, N,N'-dibenzylethylenediamine salt (XII) (675.7 g.) during 5 minutes. The reaction mixture was stirred at 10°-15° for 6 hours, Celite (250 g.) was added, then the insolubles were filtered off. The filtrate was extracted with methylene chloride (2×1.5 l.) and ether (1×1.5 l.) then concentrated in vacuo (<40°; 3–5 mm. Hg). The aqueous solution (3.8 l. volume) was clarified by filtration and diluted with ethanol (13.5 l.) resulting in the precipitation of an oil. After standing for 18 hours at room temperature, the aqueous ethanol solution was removed leaving 600 ml. of crude (V) as an orange oil. Additional hydrolyses were carried out in a similar manner to give a total of 1350 ml. of oil suitable for further transformation.

L-Aspartic acid, N—(phosphonoacetyl)—, disodium salt -0.2 H$_2$O - 0.2 sodium acetate - 0.4 acetic acid - 0.15 ethanol L-Aspartic acid, N—(phosphonoacetyl)—, tetrasodium salt (V) (1350 ml. of oil) was dissolved in glacial acetic acid (6.5 l.) at room temperature. The orange solution was stirred for 30 minutes, clarified by filtration, then diluted with ethanol (18.0 l.). The resulting mixture was stirred for 1 hour, then the solvent was removed using filter candles. The solid was suspended in ethanol (10.5 l.) and the mixture was vigorously stirred for 1 hour. The ethanol was drawn off as above, then the material was washed twice more with ethanol (10.5 l. then 6.0 l.). The solid was collected on three filters, under a nitrogen atmosphere, washed with ether (2×1.0 l./funnel), then partially dried by spin-evaporation at reduced pressure (30°-45°; aspirator then 3–5 mm Hg). The lumpy solid was thoroughly pulverized, under nitrogen, then dried in vacuo over phosphorus pentoxide (33.5 hours at room temperature and 12.5 hours at 50°) to give 945.1 g. of the analytically pure desired product.

Anal.
Calc'd. for C$_6$H$_8$NO$_8$P . 2 Na . 0.2 H$_2$O . 0.2 C$_2$H$_3$O$_2$Na . 0.4 C$_2$H$_4$O$_2$ . 0.15 C$_2$H$_6$O

|  | C | H | N | P | Na |
|---|---|---|---|---|---|
|  | 25.74 | 3.31 | 4.00 | 8.85 | 14.45 |
| Found | 25.55 | 3.35 | 4.06 | 9.19 | 14.30 |

Spectral Data:
Nuclear Magnetic Resonance (D$_2$O): δ 0.89 (t, 0.45, —CH$_3$ of ethanol); 1.78 (s, 1.8, —CH$_3$ of acetate+acetic acid); 2.54 (d, 2, —CH$_2$ α to —CH); 2.54 (d, 2, J=20.3 Hz, —CH$_2$ α to P); 3.36 (q, 0.30, —CH$_2$ of ethanol); 4.28 (t, 1, —CH)
Optical Rotation:
Observed: [α]$_D^{22}$+16.39 (c, 1.885 in water).
Chromatography:

| Thin Layer chromatography (Cellulose, Quanta/Gram Q2F Glass Plates) | |
|---|---|
| Solvent System | R$_f$ Value |
| 1. Lithium chloride (0.6 M)-ethanol-ammonium hydroxide (5:5:1) | 0.64 |
| 2. Ethanol-water (2:3) | 0.78 |
| 3. Ethanol-ammonium hydroxide-water (6:1:3) | (elongated) 0.24 |
| 4. n-Butanol-acetic acid-water (5:2:3) | (tailing) 0.28 |

Detection: Phospray (A commercial spray reagent used to visualize phosphorus-containing compounds).
Results: The compound moves as one spot in each of the solvent systems.

EXAMPLE 6

L-Aspartic acid, N—(phosphonoacetyl)—, dibenzyl ester (IV)

To a cool (10°), stirred suspension of L-aspartic acid, dibenzyl ester p-toluenesulfonate (I) (5785 g.; 11.91 moles) in dry dioxane (30.0 l.) was added, in one portion, triethylamine (3238 g.; 32.00 moles). The resulting solution was stirred for 1 hour then phosphonoacetyl chloride (III) (2236 g.; 14.11 moles) dissolved in dry dioxane (5.5 l.) was added, dropwise, during 3 hours. The temperature was maintained below 30° during the addition. The cooling bath was removed, and the reaction mixture was stirred for 1 hour. The insolubles were filtered off and washed with dioxane (12.0 l.). The filtrate was concentrated in vacuo, then the oily residue was dissolved in methylene chloride (64.0 l.). The organic solution was washed with water (6×19.0 l.), dried over sodium sulfate, then evaporated at reduced pressure to a volume of 5.0 l.

L-Aspartic acid, N—(phosphonoacetyl)—, tetrasodium salt (V)

To a cool (15°), stirred solution of sodium hydroxide (1323 g.; 33.08 moles) in water (43.0 l.) was added, in one portion, 2.4 l. of the above prepared methylene chloride solution of L-aspartic acid, N—(phosphonoacetyl)—, dibenzyl ester (IV) (2.4 l.=2400 g.; 5.512 moles). The reaction mixture was stirred at 10°-15° for 8 hours, Celite (825 g.) was added, then the insolubles were filtered off (600 g. Celite pad). The filtrate was extracted with methylene chloride (2×9.0 l.) and ether (1×9.0 l.). The aqueous solution was combined with that from an identical run and concentration in vacuo (<35°; 3-5 mm. Hg). The solution (25.0 l. volume) was clarified by filtration (400 g. Celite pad) and diluted with ethanol (88.0 l.) resulting in the precipitation of an oil. After standing for 7.5 hours at room temperature, the aqueous ethanol solution was removed leaving 4.4 l. of crude (V) as an orange oil. An additional 6695 g. of (IV) was hydrolyzed in a similar manner to give a total of 9.98 l. of oil suitable for further transformation.

L-Aspartic acid, N—(phosphonoacetyl)—, disodium salt

L-Aspartic acid, N—(phosphonoacetyl)—, tetrasodium salt (V) (4.4 l. of oil) was dissolved in glacial acetic acid (14.0 l.) at room temperature. The orange solution was stirred for 1 hour, clarified by filtration, then diluted with ethanol (44.0 l.). The resulting mixture was stirred for 1.5 hours, then the solvent was removed using filter candles. The solid was suspended in ethanol (30.0 l.), and the mixture was vigorously stirred for 2 hours. The ethanol was drawn off as above, then the material was washed by resuspension in ethanol (2×30.0 l.) and ether (1×14.0 l.). The solid was collected on two filters, under a nitrogen atmosphere, then partially dried by spin-evaporation in vacuo (30°-45°; aspirator pressure then 3-5 mm Hg). An additional 2.93 l. of oil (V) was reacted in a similar manner. The combined lumpy material was thoroughly pulverized, under nitrogen, then dried in vacuo over phosphorus pentoxide (40 hours at room temperature and 17 hours at 45°-50°) to give 4562.5 g. of a light yellow powder. The nuclear magnetic resonance spectrum and elemental analysis of this material revealed the presence of sodium acetate (0.1 mole), acetic acid (0.5 mole), and ethanol (0.15 mole). 2000 g. portion of the product was added, in portions, to 11.5 l. of vigorously stirred glacial acetic acid during 20 minutes. The mixture was stirred at room temperature for 1 hour, then the solution was clarified by filtration. The filtrate was diluted with ethanol (26.0 l.), and the resulting mixture was stirred for 2 hours. The solvent was removed (filter candles), then the solid was washed twice by resuspension in ethanol (7.0 l. then 15.0 l.), collected on a filter, and dried by spin-evaporation at reduced pressure. The white solid (1989 g.) was determined by nuclear magnetic resonance to contain acetic acid (1.25 moles) and ethanol (0.24 mole). A 1974 g. quantity of the material was dissolved in water (4.0 l.), and the aqueous solution was diluted with ethanol (16.0 l.). The resulting mixture was stirred for 30 minutes, then the precipitated oil was allowed to settle. The aqueous ethanol solution was removed, and the oil was washed once with ethanol (3.5 l.). This material, which contained acetic acid (0.03 mole) and ethanol (0.8 mole) as determined by nuclear magnetic resonance, was dissolved in water (32.0 l.). The aqueous solution was clarified by filtration then freeze-dried to give 1512.4 g. of a flocculant, yellow solid.

Anal.
Calc'd. for $C_6H_8NO_8P \cdot 2 Na \cdot H_2O \cdot 0.03\ C_2H_4O_2 \cdot 0.35\ C_2H_6O$

|   | C | H | N | P | Na |
|---|---|---|---|---|---|
|   | 24.23 | 3.68 | 4.18 | 9.24 | 13.72 |
| Found | 24.39 | 3.56 | 4.15 | 9.03 | 13.44 |

Spectral Data:
Nuclear Magnetic Resonance ($D_2O$): δ 1.19 (t, —$CH_3$ of ethanol); 2.11 (s, —$CH_3$ of acetic acid); 2.83 (d, 2, J=20 Hz, —$CH_2$ α to P); 2.87 (d, 2, —$CH_2$ α to —CH); 3.67 (q, —$CH_2$ of ethanol); 4.61 (t, 1, —CH).

Optical Rotation:
Observed: $[\alpha]_D^{22} + 14.68$ (c, 1.873 in water).

Chromatography:

| Thin Layer Chromatography (Cellulose, Quanta/Gram Q2F Glass Plates) | |
|---|---|
| Solvent System | $R_f$ Value |
| 1. Lithium chloride (0.6 M)-ethanol-ammonium hydroxide (5:5:1) | 0.66 |
| 2. Ethanol-water (2:3) | 0.83 |
| 3. Ethanol-ammonium hydroxide-water (6:1:3) | (elongated) 0.31 |
| 4. n-Butanol-acetic acid-water (5:2:3) | 0.28 |

Detection: Phospray (A commercial spray reagent used to visualize phosphorus-containing compounds).

Results: The compound moves as one spot in each of the solvent systems.

Scale-up development for the preparation of the pure salt has overcome some potentially serious manipulative problems. The cyclohexylamine salt of dibenzyl PALA is prepared by adding from about 0.9 to about 1.0 equivalent of cyclohexylamine to an acetone solution of dibenzyl PALA. The product is insoluble in acetone whereas a large percentage of impurities remain in solution. The purity of the product is upgraded to an acceptable level by recrystallization from absolute methanol.

The purity of the product is upgraded to an acceptable level by recrystallization from absolute methanol.

Difficulties are encountered in the use of dioxane for the preparation of dibenzyl PALA. Triethylamine hydrochloride is an insoluble by-product of the reaction, and large volumes of solvent are required in order to maintain sufficient stirring. In addition, the reaction is exothermic, and the use of dioxane limits the extent of cooling to ~12°, which is the temperature at which dioxane freezes.

The solvent substituted for dioxane in this reaction was methylene chloride. This solvent offers the following advantages: (a) It is nonflammable; (b) It allows for a lower cooling temperature; (c) The volume of solvent is reduced in half; (d) The removal of triethylamine hydrochloride by filtration is eliminated since it is soluble in the reaction mixture; and (e) The evaporation of the solvent prior to work-up is no longer necessary.

Additional process improvements include the fact that the cyclohexylammonium salt is hydrolyzed directly to the tetrasodium PALA. This eliminates the extra manipulation of releasing the dibenzyl PALA from the amine salt prior to hydrolysis.

A final point is that the volume of water required for the hydrolysis has been reduced by 63% over that used in the initial synthetic work. This, of course, allows for larger scale runs to be made using the same size equipment. At the bench scale, using as a maximum 50 l. flasks, this procedure has been used to prepare disodium PALA in ~2 kg. lots. Incorporating all of the described modifications, a run using 50 and 100 gallon Pfaudlers has been successfully carried out. At full scale, ~15 kg. of the target material can be produced per run using this size equipment.

The process, as currently developed, is limited only by the size of the equipment.

By the present methods, the purity of the desired disodium PALA material has been upgraded to a level satisfactory for parenteral administration in a suitable vehicle for treatment of human cancer, particularly for investigational purposes on a large scale. This was accomplished by (1) completely eliminating acetic acid and sodium acetate through a turbulent flow precipitation; and (2) isolating dibenzyl PALA as the cyclohexylammonium salt. In addition, the procedure has been optimized for ease of scale-up, and the problems of process manipulations have been solved.

EXAMPLE 7

Phosphonoacetyl chloride (III)

To a stirred mixture of phosphonoacetic acid (II) (2000 g.; 14.28 moles), N,N-dimethylformamide (208.8 g.; 2.856 moles), and dioxane (7.15 l.) was added, dropwise, thionyl chloride (3568 g.; 29.99 moles) during 1.5 hours. The temperature was maintained below 30° during the addition. The resulting solution was heated at 45° for 2.5 hours then cooled to 5°. Water (283 ml.; 15.7 moles) dissolved in dioxane (2.5 l.) was then added, dropwise, over a period of 2 hours. The temperature was kept below 10° during the addiion. This solution of acid chloride (III) was stirred at 5°–10° for 40 minutes then used in the following reaction without further characterization. A second chlorination was carried out concurrently, under the same conditions, using identical quantities of reactants.

L-Aspartic acid, N—(phosphonoacetyl)—, dibenzyl ester (IV)

A stirred suspension of L-aspartic acid, dibenzyl ester p-toluenesulfonate (I) (4625 g.; 9.525 moles) in dioxane (20.0 l.) was cooled to 15°, then triethylamine (4820 g.; 47.63 moles) was added, in a thin stream, during 1 hour. The resulting solution was stirred for 20 minutes, then the above solution of phosphonoacetyl chloride (III), prepared from 14.28 moles of the corresponding acid, was added, dropwise, over a period of 5 hours. The temperature was maintained below 20° during the addition. Additional triethylamine (1162 g.; 11.48 moles) was added and the reaction mixture was stirred for 1 hour. After standing for 8 hours at room temperature, the mixture was diluted with acetone (5.5 l.), stirred for 15 minutes, then the insolubles were collected on a filter and washed with dioxane (10.0 l.). A second reaction was carried out concurrently, under the same conditions, using identical amounts of materials. The filtrates from the two runs were combined and spin-evaporated in vacuo. The residue (orange, viscous oil) was dissolved in methylene chloride (110.0 l.), then the organic solution was gently washed with water (6×30.0 l.). After drying the solution over sodium sulfate (11.3 kg.) and magnesium sulfate (2.3 kg.), the insolubles were filtered off (Celite pad), and the filtrate was evaporated in vacuo to constant weight; yield of dibenzyl PALA (IV) 7970 g. (96.1%). This yellow, viscous oil was suitable for further transformation.

L-Aspartic acid, N—(phosphonoacetyl)—, dibenzyl ester, cyclohexylamine salt

Cyclohexylamine (1815 g.; 18.30 moles) was added, dropwise, to a cold (7°), stirred solution of L-aspartic acid, N—(phosphonoacetyl)—, dibenzyl ester (IV) (7970 g.; 18.30 moles) in acetone (24.0 l.) during 1.25 hours. The temperature was maintained below 15° during the addition. The cooling bath was removed, and the resulting mixture was stirred for 1 hour. The mixture was stored at room temperature for 6 hours, then the precipitated solid was collected on a filter, washed with acetone (15.0 l), and dried: yield, 4932 g.; m.p., 176.5°–177.5°. This material was recrystallized from boiling methanol (35.0 l.) then dried to give 1663 g. of the purified salt; m.p., 178°–181°.

The mother liquor was concentrated in vacuo to a volume of 20.0 . The solution was diluted with acetone (16.0 l.) and cooled (−10°) to give an additional 967 g. of product; m.p., 177°–180°. A third crop of material (429 g.) was obtained by evaporating the above methanol-acetone filtrate to near dryness and suspending the residue in acetone (5.0 l.); total amount of the purified amine salt suitable for further transformation, 3059 g. (62.0% recovery).

L-Aspartic acid, N—(phosphonoacetyl)—, tetrasodium salt (V)

To a cold (5°), stirred solution of sodium hydroxide (1291 g.; 32.28 moles) in water (20.5 l.) was added, in portions, during 30 minutes, L-aspartic acid, N—(phosphonoacetyl)—, dibenzyl ester, cyclohexylamine salt (3059 g.; 5.378 moles).

The reaction mixture was stirred at 5°–15° for 3.5 hours, then extracted with methylene chloride (2×8.5 l.) and ether (1×8.5 l.). The aqueous solution was clarified by filtration, concentrated in vacuo (<35°; 3–5 mm. Hg) to a volume of 14.6 l., then diluted with ethanol (51.4 l.). The resulting mixture was stirred for 1 hour and stored at room temperature for 12 hours. The aqueous ethanol solution was removed giving crude (V) as a light yellow oil suitable for further transformation.

L-Aspartic acid, N—(phosphonoacetyl)—, disodium salt

Glacial acetic acid (8.0 .) was added to the above precipitated oil [crude L-aspartic acid, N—(phosphonoacetyl)—, tetrasodium salt (V) prepared from 3059 g. of the amine salt]. The mixture was stirred at room temperature for 30 minutes, then a gelatinous insoluble was filtered off. The clear, light yellow filtrate was diluted with ethanol (24.0 .). The resulting mixture was stirred for 1.75 hours, then the precipitated material was collected on a filter. The solid was suspended in ethanol (14.5 l.), and the mixture was vigorously stirred for 1 hour. The product was collected on four filters then partially dried by spin-evaporation in vacuo (30°–45°; aspirator pressure then 3–5 mm. Hg). The lumpy material (2870 g.) was dissolved in water (5.25 l.), the solution was clarified by filtration, then the filtrate (~6.9 l. volume) was diluted with ethanol (21.0 l.). The resulting mixture was stirred for 30 minutes, then the precipitated oil was allowed to steele (1 hour). The aqueous ethanol solution was removed, and the oil was washed once with ethanol (4.3 l.). This material was dissolved in water (8.15 l.), and the solution (9.8 l.) was dissolved into three portions (two of 4.0 .; one of 1.8 l.). Each portion was added, during 13 hours, to the vortex of vigorously stirred ethanol (10×aqueous volume: 2×40.0 L.; 2×18.0 l.). After stirring the mixtures for 2 hours, the water-ethanol solutions were siphoned off, and the solid from the three precipitations was combined. The material was stirred for 30 minutes in ethanol (10.0 l.), collected on a filter, then dried to constant weight in vacuo at room temperature over phosphorous pentoxide. The dried product (1748.0 g.) was passed through a 150μ, stainless steel sieve and thoroughly blended to give the disodium PALA as a white powder.

Anal.
Calc'd. for $C_6H_{7.6}NO_8P \cdot 2.4\ Na \cdot 2\ H_2O \cdot 0.5\ C_2H_6O$

|  | C | H | N | P | Na |
|---|---|---|---|---|---|
|  | 22.91 | 4.01 | 3.82 | 8.44 | 15.04 |
| Found | 23.16 | 3.76 | 3.79 | 8.57 | 15.18 |

Sodium analysis indicates a composition of
60% di-Na PALA
40% tri-Na PALA
Based on the empirical formula,
% $H_2O$ = 9.8%
% EtOH = 6.3%
Spectral Data:
Nuclear Magnetic Resonance ($D_2O$): δ1.17 (t, 1.5, —$CH_3$ of ethanol); 2.74 (d, 2, —$CH_2$ α to —CH); 2.77 (d, 2, J=20 Hz, —$CH_2$ α to P); 3.63 (q, 1, —$CH_2$ of ethanol); 4.48 (t, 1 —CH).
Optical Rotation:
Observed: $[\alpha]_D^{22.5}$ +14.73 (c, 2.098 in water).
Chromatogeaphy:

| | Thin Layer Chromatography (Cellulose, Quanta/Gram Q2F Glass Plates) | |
|---|---|---|
| | Solvent System | $R_f$ Value |
| 1. | Lithium chloride (0.6 M)-ethanol-ammonium hydroxide (5:5:1) | 0.52 |
| 2. | Ethanol-water (2:3) | 0.72 |
| 3. | Ethanol-ammonium hydroxide-water (6:1:3) | 0.16 (elongated) |
| 4. | n-Butanol-acetic acid-water (5.2:3) | 0.22 (tailing) |

Detection:
(a) Ninhydrin
(b) Phospray
Results: The compound moves as one phospray positive spot in each of the solvent systems. No aspartic acid was observed on spraying with ninhydrin.

EXAMPLE 8

Phosphonoacetic acid, P,P-diethyl ester

Triethyl phosphonoacetate (89.7 g.; 0.400 mole) was added, in one portion, to potassium hydroxide (0.408 mole; 26.1 g. of 87.6% pure material) dissolved in ethanol (450 ml.) and water (150 ml.). The solution was stirred at room temperature for 22 hours then spin-evaporated in vacuo (bath temperature <25°; 3-5 mm. Hg). The residue was suspended in ether (400 ml.). The crystalline material, potassium salt, was collected on a filter then dissolved in water (300 ml.).

The stirred solution was cooled to 5°, then concentrated hydrochloric acid (33 ml.) was added, dropwise, during 15 minutes. The temperature was maintained below 10° during the addition. The solution was stirred at 5°-10° for 30 minutes then concentrated in vacuo (bath temperature <25°; 3-5 mm. Hg). The residue was suspended in acetone (350 ml.). The insoluble potassium chloride was filtered off, and the filtrate was evaporated at reduced pressure. Ether (500 ml.) was added to the residual oil. The resulting mixture was cooled to 10°, and the insolubles were filtered off. The filtrate was decolorized with charcoal, dried over magnesium sulfate, then concentrated in vacuo to give 69.3 g. (88.2%) of product as a pale yellow oil. This material was suitable for further transformation.

Phosphonoacetyl chloride, P,P-diethyl ester

Oxalyl chloride (63.5 g.; 0.500 mole) dissolved in dry benzene (100 ml.) was added, dropwise, to a cool (10°), stirred solution of phosphonoacetic acid, P,P-diethyl ester (19.6 g.; 0.100 mole) in dry benzene (350 ml.) during 45 minutes. The temperature was maintained at 5°-10° during the addition. The cooling bath was removed, and the solution was stirred for 2 hours. The volatiles were removed in vacuo, then the residue was co-evaporated with benzene (2×50 ml.) to give the acid chloride as a yellow liquid. This material was used in the following reaction without further characterization.

L-Aspartic acid, N—(phosphonoacetyl)—, dibenzyl ester, P,P-diethyl ester

To a cool (15°), stirred suspension of L-aspartic acid, dibenzyl ester p-toluenesulfonate (53.4 g.; 0.110 mole) in dioxane (325 ml.) was added, dropwise, triethylamine (21.3 g.; 0.210 mole) during 10 minutes. The resulting solution was stirred at 10°-15° for 15 minutes, then a solution of acid chloride, prepared from 0.100 mole of acid in dioxane (100 ml.) was added, dropwise, during 50 minutes. The temperature was maintained below 15° during the addition. The cooling bath was removed, and the reaction mixture was stirred for 2 hours. The insoluble material was collected on a filter then washed with dioxane (50 ml.) and ether (100 ml.). The filtrate was spin-evaporated in vacuo, and the residue was dissolved in benzene (500 ml.). The organic solution was washed with water (4×150 ml.), decolorized with charcoal (10 g.), dried over magnesium sulfate, then concentrated in vacuo to an oil; yield, 51.6 g. (>100%). A 22.8 g. portion of the crude product was dissolved in ethanol (80 ml.). The solution was added, in one portion, to AG50W-X8 (hydrogen form) cation exchange resin (550 ml.) suspended in ethanol (200 ml.), and the mixture was stirred at room temperature for 9 hours. The resin was collected on a filter and washed with ethanol (250 ml.), then the filtrate was evaporated in vacuo. The oily residue was dissolved in benzene (400 ml.), then the solution was dried over magnesium sulfate and spin-evaporated at reduced pressure. The material was dried to constant weight in vacuo to give 19.7 g. (86.5% recovery) of tlc homogeneous product (silica gel; acetone-petroleum ether (b.p., 30°-60°) (2:3) or ethyl acetate). This viscous, yellow oil was suitable for further transformation.

L-Aspartic acid, N—(phosphonoacetyl)—, P-ethyl ester, disodium salt, monohydrate To a cool (10°), stirred solution of L-aspartic acid, N—(phosphonoacetyl)—, dibenzyl ester, P,P-diethyl ester (19.7 g.; 0.0400 mole) in absolute ethanol (100 ml.) was added, dropwise, sodium hydroxide (5.00 g.; 0.125 mole) dissolved in absolute ethanol (60 ml.) during 20 minutes. The temperature was maintained below 15° during the addition. The solution was stirred at 10°-15° for 45 minutes then heated at reflux for 30 minutes. An additional 3.2 g. (0.080 mole) of sodium hydroxide dissolved in ethanol (200 ml.) was added, and the mixture was refluxed for 2.5 hours. The resulting solid was collected on a filter, washed by suspension in ethanol (70 ml.) and ether (150 ml.), then dried. This tan powder (16.4 g.) was dissolved in hot (75°), glacial acetic acid (30 ml.). The solution was cooled to room temperature, diluted with ethanol (50 ml.), then clarified by filtration. Ethanol (300 ml.) was added to the filtrate, and the resulting mixture was cooled. The precipitated solid was collected on a filter, successively washed by suspension in ethanol (350 ml.), acetone (250 ml.), and ether (250 ml.), then dried; yield of product, 9.2 g. (66.6%). An 8.3 g. portion of this material, contaminated with acetic acid (determined by N.M.R.), was suspended in ethanol (200 ml.). The stirred suspension was heated at reflux for 15 minutes then cooled to room temperature. This heating-cooling process was repeated two more times, then the solid was collected on a filter. The above washing procedure was performed a total of three times. The white solid was dried to constant weight in vacuo at 40° over phosphorus pentoxide to give 7.2 g. (86.7% recovery) of analytically pure product, disodium PALA, P-ethyl ester.H$_2$O. The compound moves as one spot on cellulose (Quanta/Gram Q2F glass plates) developed with ethanol-water (2:3) ($R_f$=0.80), ethanol-ammonium hydroxide-water (6:1:3) ($R_f$=0.42), or n-butanol-acetic acid-water (5:2:3) ($R_f$=0.40); detection by Phospray.

Anal.
Calc'd. for C$_8$H$_{12}$NO$_8$P . 2Na . H$_2$O

|  | C | H | N | P | Na |
|---|---|---|---|---|---|
|  | 27.84 | 4.09 | 4.06 | 8.97 | 13.32 |
| Found | 27.71 | 4.13 | 4.07 | 8.86 | 13.45 |

Spectral Data:
Infrared (Nujol); Major bands: 3300, 2950, 2920, 2860, 1700, 1640, 1600, 1455, 1405, 1375, 1215, 1045, 935, 760 cm$^{-1}$.

Nuclear Magnetic Resonance (D$_2$O): δ1.28 (t, 3, —CH$_3$ of ethyl group); 2.82 (d, 2, —CH$_2$ α to —CH); 2.85 (d, 2, J=20.0 Hz, —CH$_2$ α to P); 4.00 (5 line m, 2, —CH$_2$ of ethyl group); 4.57 (t, 1, —CH).

EXAMPLE 9

L-Aspartic acid, N—(phosphonoacetyl)—, dibenzyl ester, disodium salt, tetrahydrate A solution of L-aspartic acid, N—(phosphonoacetyl)—, dibenzyl ester (26.7 g.; 0.610 mole) and triethylamine (25.2 ml.; 0.180 mole) in acetone (180 ml.) was stirred at room temperature for 1 hour. The volatiles were removed in vacuo, then the semi-solid residue was dissolved in acetone (300 ml.). Sodium iodide (27.0 g.; 0.180 mole) dissolved in acetone (150 ml.) was then added, and the reaction solution was heated at reflux for 3 hours. The solvent was removed by spin-evaporation at reduced pressure, then the residue was suspended in water (300 ml.). The solid material was collected on a filter, washed with methanol (200 ml.) and acetone (100 ml.), then dried to constant weight to give 7.7 g. (26%) of analytically pure product; m.p., >300°. The compound either streaks or remains at the base line on tlc. A sample was therefore converted to the free acid with hydrochloric acid. This material moves as one spot on cellulose (Quanta/Gram Q2F glass plates) developed with methanol-water (9:1), ethanol-acetone-water (5:4:1), or ethanol-ether (1:1).

Anal.
Calc'd. for C$_{20}$H$_{20}$NO$_8$P . 2Na . 4H$_2$O

|  | C | H | N | P | Na |
|---|---|---|---|---|---|
|  | 43,57 | 5.12 | 2.54 | 5.62 | 8.34 |

Anal.
Calc'd. for C$_{20}$H$_{20}$NO$_8$P . 2Na . 4H$_2$O

|  | C | H | N | P | Na |
|---|---|---|---|---|---|
| Found | 43.95 | 4.69 | 2.50 | 5.57 | 8.31 |

Spectral Data:
Infrared (Nujol); Major bands: 3600, 3360, 2960, 2920, 2860, 1740, 1720, 1635, 1540, 1450, 1375, 1340, 1280, 1200, 1130, 1045, 965, 724 cm$^{-1}$.

EXAMPLE 10

L-Aspartic acid, diethyl ester, hydrochloride

Hydrogen chloride was bubbled into a stirred suspension of L-aspartic acid (133 g.; 1.00 mole) in absolute ethanol (1.95 l.) at room temperature for 2 hours. The resulting solution was heated at reflux for 5 hours, cooled to room temperature, then evaporated in vacuo. The residue was dissolved in benzene (500 ml.). The solution was heated to reflux, and the water present was removed by means of a Dean-Stark trap. The solution was then concentrated at reduced pressure to an oil which slowly crystallized on standing. The solid was suspended in ether (1.3 l.), collected on a filter, washed with ether (800 ml.), then dried; yield of L-aspartic acid, diethyl ester, hydrochloride, 216 g. (95.7%); m.p., 99°–103°. This material was recrystallized from 1.25 l. of acetone-ether (4:1) to give 164.6 g.(76.2% recovery) of product suitable for further transformation; m.p., 106.5°–107.5°.

L-Aspartic acid, N—(phosphonoacetyl)—, tetraethyl ester

To a cool (10°), stirred suspension of L-aspartic acid, diethyl ester, hydrochloride (19.2 g.; 0.0850 mole) in dioxane (350 ml.) was added, dropwise, triethylamine (18.2 g.; 0.180 mole) during 20 minutes. The mixture was stirred at 10° for 15 minutes, then a solution of phosphonoacetyl chloride, P,P-diethyl ester, prepared from 0.090 mole of acid, in dioxane (90 ml.) was added, dropwise, during 1 hour. The temperature was maintained at 8°–10° during the addition. The cooling bath was removed, and the reaction mixture was stirred for 3.5 hours. The insoluble material was collected on a filter then washed with dioxane (100 ml.) and ether (200 ml.). The filtrate was spin-evaporated in vacuo, and the residue was dissolved in ethyl acetate (300 ml.). The organic solution was washed with water (3×100 ml.), dried over magnesium sulfate, then concentrated in vacuo to an oil; yield of L-aspartic acid, N—(phosphonoacetyl)—, tetraethyl ester, 31.1 g. (99.6%). A 25.9 g. portion of the product was dissolved in ether (500 ml.), and the solution was extracted with water (5×150 ml.). The aqueous extracts were combined and concentrated at reduced pressure to an oil. This pale yellow material was dried in vacuo over phosphorus pentoxide to give 20.1 g. (77.6% recovery) of analytically pure product. The compound moves as a single spot on silica gel (Eastman Chromagram Sheet 13181) developed with acetone, chloroform, or ethyl acetate; detection by iodine vapors.

|  | C | H | N | P |
|---|---|---|---|---|
| Anal. |  |  |  |  |
| Calc'd. for C$_{14}$H$_{26}$NO$_8$P | 45.77 | 7.13 | 3.81 | 8.43 |

| Anal. | C | H | N | P |
|---|---|---|---|---|
| Found | 45.88 | 7.11 | 3.81 | 8.50 |

Spectral Data:

Infrared (Neat); Major bands: 3260, 2980, 2920, 2900, 1730, 1670, 1545, 1525, 1440, 1390, 1365, 1335, 1230, 1200, 1090, 1040, 1015, 955, 850 cm$^{-1}$.

Nuclear Magnetic Resonance (CDCl$_3$): δ1.23 (m, 12, —CH$_3$ of ethyl groups); 2.83 (d of d. 2, —CH$_2$ α to —CH); 2.85 (d, 2, J=20.0 Hz, —CH$_2$ α to P); 4.08 (m, 8, —CH$_2$ of ethyl groups); 4.77 (broad m, 1, —CH); 7.37 (broad d, 1, —NH).

Optical Rotation:

Observed: $[\alpha]_D^{24}$ −6.05 (c, 3.849 in water).

EXAMPLE 11

L-Aspartic acid, dimethyl ester. hydrochloride

To absolute methanol (1.90 l.; 1.50 kg.; 46.8 moles) being stirred at −5° was added, dropwise, thionyl chloride (357 g.; 3.00 moles) during 2 hours. The temperature was maintained between 0° and −5° during the addition. The solution was stirred at 0° to −5° for 1.5 hours. then L-aspartic acid (133 g.; 1.00 mole) was added, in portions, over a period of 35 minutes. The solution was stirred at −5° for 2.5 hours and at room temperature for 16 hours. The volatiles were removed in vacuo. then the oily residue was evaporated at reduced pressure with benzene (4×175 ml.). The resulting solid was collected on a filter, washed with ether (400 ml.), and dried. The crude material (190.4 g.) was recrystallized from 3.5 l. of boiling acetone to give 135 g. (68.3%) of product suitable for further transformation; m.p., 117°-119°.

L-Aspartic acid, N—(phosphonoacetyl)—, dimethyl ester, P,P-diethyl ester

To a cool (10°), stirred suspension of L-aspartic acid, dimethyl ester, hydrochloride (18.8 g.; 0.0950 mole) in dioxane (350 ml.) was added, dropwise, triethylamine (20.2 g.; 0.200 mole) during 15 minutes. The mixture was stirred at 10° for 15 minutes, then phosphonoacetyl chloride, P,P-diethyl ester, prepared from 0.100 mole of the acid , dissolved in dioxane (100 ml.) was added, dropwise, during 1 hour. The temperature was maintained at 5°-10° during the addition. The cooling bath was removed, and the reaction mixture was stirred for 1.25 hours. The insolubles were collected on a filter, washed with dioxane (100 ml.) and ether (200 ml.). then the filtrate was concentrated in vacuo. The oily residue was dissolved in benzene (100 ml.) and ether (400 ml.), then the organic solution was washed with water (4×150 ml.). The aqueous solutions were combined, saturated with sodium chloride, and extracted with ethyl acetate (3×500 ml.). The combined extracts were dried over magnesium sulfate then evaporated in vacuo to give 33.2 g. (103%) of crude product as a yellow oil. An 18.0 g. portion of the material was dissolved in water (50 ml.), and the solution was applied to an AG50W-X8 (hydrogen form) cation exchange resin column (3.8 cm.×15 cm.). The column was eluted with 500 ml. of water. Fractions containing the desired product, as determined by tlc, were combined and spin-evaporated in vacuo. The residue was dissolved in chloroform (120 ml.), and the solution was dried over magnesium sulfate. The solvent was removed at reduced pressure, then the pale yellow oil was dried in vacuo over phosphorus pentoxide to give 14.4 g. (80% recovery) of analytically pure L-aspartic acid, N—(phosphonoacetyl)—, dimethyl ester, P,P-diethyl ester. The compound moves as a single spot on silica gel (Eastman Chromagram Sheet 13181) developed with acetone, chloroform, or ethyl acetate; detection by iodine vapors.

| Anal. | C | H | N | P |
|---|---|---|---|---|
| Calc'd. for C$_{12}$H$_{22}$NO$_8$P | 42.48 | 6.54 | 4.12 | 9.13 |
| Found | 42.50 | 6.51 | 4.09 | 9.06 |

Spectral Data:

Infrared (Neat); Major bands: 3260, 2980, 2950, 1735, 1665, 1530, 1435, 1365, 1220, 1160, 1040, 1015, 955 cm$^{-1}$.

Nuclear Magnetic Resonance (CDCl$_3$): δ1.35 (t, 6, —CH$_3$ of ethyl groups); 2.88 (d, 2, —CH$_2$ α to —CH); 2.90 (d, 2, J=21.5 Hz. —CH$_2$ α to P); 3.65 (s, 3, —CH$_3$); 3.70 (s, 3, —CH$_3$); 4.08 (5 line m. 4, —CH$_2$ of ethyl groups); 4.80 (broad m, 1, —CH); 7.47 (broad d, 1, —NH).

Optical Rotation

Observed: $[\alpha]_D^{24}$ −6.89 (c, 3.183 in water).

EXAMPLE 12

L-Aspartic acid, N—(phosphonoacetyl)—, piperazine salt (1:2.5), tetrahydrate-0.5C$_2$H$_5$OH To a cool (10°), stirred solution of L-aspartic acid, N—(phosphonoacetyl)—, (10.2 g.; 0.0400 mole) in water (60 ml.) was added, dropwise, piperazine (15.2 g.; 0.176 mole) dissolved in water (100 ml.) during 35 minutes. The temperature was maintained below 15° during the addition. The solution was stirred at 10°-15° for 1 hour then spin-evaporated in vacuo (<35°; 2-5 mm. Hg). The semi-solid residue was triturated with ethanol (2×200 ml.) then dissolved in water (60 ml.). Charcoal (1 g.) was added, and the mixture was stirred at room temperature for 25 minutes. The insolubles were filtered off. then the filtrate was added, dropwise, to vigorously stirred ethanol (2.0 l.) during 40 minutes. The resulting solid was collected on a filter, washed with acetone (200 ml.) and dried to give 5.8 g. (25.6%) of L-aspartic acid, N—(phosphonoacetyl)—, piperazine salt (1:2.5), tetrahydrate-0.5C$_2$H$_5$OH; m.p. 92°-95°; 111°-115° (sealed capillary). The compound moves as one major spot on cellulose (Quanta/Gram Q2F glass plates) developed with ethanol-ammonium hydroxide-water (6:1:3) ($R_f$=0.34), n-butanol-acetic acid-water (5:2:3) ($R_f$=0.25), or ethanol-water (2:3) ($R_f$=0.79); detection by Phospray.

Anal.
Calc'd. for C$_6$H$_{10}$NO$_8$P . 2.5 C$_4$H$_{10}$N$_2$ . 4 H$_2$O . 0.5 C$_2$H$_5$OH

|  | C | H | N | P |
|---|---|---|---|---|
|  | 36.10 | 8.20 | 14.86 | 5.48 |
| Found | 35.74 | 7.20 | 14.62 | 5.48 |

Spectral Data:

Infrared (Nujol); Major bands: 3340, 3270, 2950, 2920, 2850, 2720, 1645, 1625, 1580, 1460, 1380, 1295. 1050, 950 cm$^{-1}$.

Nuclear Magnetic Resonance (D$_2$O): δ0.88 (t, 1.5, —CH$_3$ of EtOH); 2.40 (3 line m. 4, —CH$_2$ α to P+—CH$_2$ of aspartate); 3.12 (s. 20. —CH$_2$ of piperazine ring); 3.33 (q. 1. —CH$_2$ of EtOH); 4.10 (broad t, 1, —CH of aspartate).

EXAMPLE 13

L-Aspartic acid, N—(phosphonoacetyl)—

To a cool (10°), stirred solution of sodium hydroxide (289 g.; 7.23 moles) in 9.35 l. of water was added. in one portion, L-aspartic acid. N—(phosphonoacetyl)—. dibenzyl ester (523 g.; 1.20 moles). The mixture was stirred at 10°-15° for 7 hours, then the insolubles were filtered off. The filtrate was concentrated in vacuo to a volume of 3.0 l. then extracted with methylene chloride (1×1.36 l.) and ether (1×1.36 l.). The aqueous solution was added to 12.0 l. of ethanol resulting in the precipitation of a semi-solid. After decantation, the material was dissolved in water (680 ml.), and the solution was applied to an AG50W-X8 (hydrogen form) cation exchange resin column (8 cm.×46 cm.). The column was eluted with 2.7 l. of water (18 fractions of 150 ml. each). Fractions 8–16, which contained the desired product as determined by tlc, were combined and evaporated in vacuo (bath temperature <30°). The oily residue was dissolved in acetone (2.0 l.), charcoal (50 g.) was added. and the mixture was stirred at room temperature for 18 hours. The insolubles were filtered off, then the filtrate was spin-evaporated at reduced pressure. The residue was dried in vacuo at room temperature over phosphorus pentoxide for 18 hours to give 220 g. (71.8%) of the tetraacid. This semi-solid material was suitable for further transformation.

L-Aspartic acid, N—(phosphonoacetyl)—, calcium salt (1:1.5).2.5 H$_2$O

To a cool (10°), stirred solution of L-aspartic acid. N—(phosphonoacetyl)— (20.4 g.; 0.0800 mole) in water (300 ml.) was added, in portions, calcium carbonate (17.6 g.; 0.176 mole) during 30 minutes. The reaction mixture was stirred at room temperature for 21 hours, then the insoluble material (7.2 g.) was collected on a filter and washed with water (50 ml.). Charcoal (5 g.) was added to the aqueous filtrate, and the mixture was stirred for 35 minutes at room temperature. The insolubles were filtered off. and the filtrate was diluted with acetone (600 ml.). The resulting solid was collected on a filter. washed with acetone (200 ml.) and ether (200 ml.), then dried. This material (24.7 g.) was suspended in water (12 ml.), and the mixture was vigorously stirred for 10 minutes. The insolubles were filtered off, then the filtrate was added to acetone (350 ml.). The precipitated solid was collected on a filter, washed with acetone (200 ml.), then dried to give 10.8 g. (37.8%) of analytically pure L-aspartic acid, N—(phosphonoacetyl)—, calcium salt 2.5 H$_2$O; m.p., >280°.

Anal.
Calc'd. for C$_6$H$_7$NO$_8$P . 1.5 Ca . 2.5 H$_2$O

|  | C | H | N | P | Ca |
|---|---|---|---|---|---|
|  | 20.17 | 3.39 | 3.92 | 8.67 | 16.83 |
| Found | 20.28 | 3.09 | 3.88 | 8.63 | 16.85 |

Spectral Data:
Infrared (Nujol); Major bands: 3530, 3380, 2950, 2920, 2850, 1590, 1455, 1375, 1140, 1110, 1070, 975 cm$^{-1}$.

Nuclear Magnetic Resonance (D$_2$O): δ2.62 (3 line m, 4; —CH$_2$ α to P+—CH$_2$ α to —CH); 4.35 (t, 1, —CH). Optical Rotation:

Observed: $[\alpha]_D^{22}$+8.38 (c, 3.113 in water).
Chromatography:

| Thin Layer Chromatography (Cellulose, Quanta/Gram Q2F Glass Plates) | | |
|---|---|---|
| Solvent System | R$_f$ Value (Calcium Salt) | R$_f$ Value (Free Acid) |
| 1. n-Butanol-acetic acid-water (5:2:3) | 0.18 | 0.29 |
| 2. Ethanol-ammonium hydroxide-water (6:1:3) | 0.00 | 0.13 |
| 3. Ethanol-water (2:3) | 0.84 | 0.75 |

Detection: Phospray (A commercial spray reagent used to visualize phosphorus containing compounds).
Results: The free acid was liberated from the calcium salt by acidification with hydrochloric acid. A base line spot was observed for the acid in each of the solvent systems and for the calcium salt in system 3.

EXAMPLE 14

L-Aspartic acid, N—(phosphonoacetyl)—, cyclohexylamine salt dihydrate

To a cool (15°), stirred solution of L-aspartic acid. N—(phosphonoacetyl)—, (5.1 g.; 0.020 mole) in water (50 ml.) was added, dropwise, cyclohexylamine (8.7 g.; 0.088 mole) dissolved in water (15 ml.) during 15 minutes. The temperature was maintained below 20° during the addition. The solution was stirred at room temperature for 30 minutes then diluted with acetone (850 ml.). The resulting solid was collected on a filter, washed with acetone (200 ml.), and air dried. The crude product was dissolved in water (100 ml.). charcoal (5 g.) was added, and the mixture was stirred at room temperature for 1.5 hours. The insolubles were filtered off. then the filtrate was added to vigorously stirred acetone (1.3 l.). The precipitated solid was collected on a filter, washed with acetone (400 ml.), then dried to give 8.0 g. (65.7%) of L-aspartic acid, N—(phosphonoacetyl)—, cyclohexylamine salt dihydrate; m.p., 167.5°-170.5°. The compound moves as one spot on cellulose (Quanta/Gram Q2F glass plates) developed with ethanol-ammonium hydroxide-water (6:1:3) (R$_f$=0.38), n-butanol-acetic acid-water (5:2:3) (R$_f$=0.33), or ethanol-water (2:3) (R$_f$=0.82); detection by Phospray.

Anal.
Calc'd. for C$_6$H$_{10}$NO$_8$P . 3.2 C$_6$H$_{11}$NH$_2$ . 2 H$_2$O

|  | C | H | N | P |
|---|---|---|---|---|
|  | 49.74 | 9.21 | 9.67 | 5.09 |
| Found | 50.12 | 8.37 | 9.44 | 5.07 |

Spectral Data:
Infrared (Nujol); Major bands: 3210, 3050, 2950, 2920, 2860, 2670, 2620, 1640, 1575, 1545, 1460, 1450, 1400, 1380, 1300, 1145, 1115, 1040 cm$^{-1}$.

Nuclear Magnetic Resonance (D$_2$O): δ1.50 (m, 32, —CH$_2$ of cyclohexane ring); 2.57 (3 line m, 4, —CH$_2$ α to P+—CH$_2$ of aspartate); 2.97 (broad s, 3.2, —CH of cyclohexane ring); 4.22 (d of d, 1, —CH of aspartate).

EXAMPLE 15

L-Aspartic acid, N—(phosphonoacetyl)—, dibenzyl ester, cyclohexylamine salt 138 g. (0.317 mole) of L-aspartic acid, N—(phosphonoacetyl)—, dibenzyl ester was dissolved in acetone (500 ml.). The stirred solution was cooled to 10°, then cyclohexylamine (69.2 g.; 0.700 mole) was added, dropwise, during 30 minutes. The resulting suspension was stirred at room temperature for 18 hours. The precipitated solid was collected on a filter, washed with acetone (500 ml.) and ether (400 ml.) then dried to give 47.2 g. of N-(phosphonoacetyl-L-aspartic acid, dibenzyl ester, cyclohexylamine salt. A 24.8 g. portion of the material was recrystallized from boiling methanol (500 ml.) to give 18.3 g. (73.8% recovery) of the purified cyclohexylamine salt; m.p., 186°–188°.

We claim:

1. A compound which is N-(phosphonoacetyl)-L-aspartic acid, disodium salt.

* * * * *